(12) United States Patent
Hourigan et al.

(10) Patent No.: US 9,414,587 B2
(45) Date of Patent: *Aug. 16, 2016

(54) SOLUBILIZED MAGNOLOL ANALOGS

(75) Inventors: Regina Hourigan, Metuchen, NJ (US); Jeffrey Mastrull, Flemington, NJ (US); Jairajh Mattai, Piscataway, NJ (US); James Masters, Ringoes, NJ (US)

(73) Assignee: Cologne-Palmolive Company, New York, NY (US)

( * ) Notice: Subject to any disclaimer, the term of this patent is extended or adjusted under 35 U.S.C. 154(b) by 2 days.

This patent is subject to a terminal disclaimer.

(21) Appl. No.: 14/362,903

(22) PCT Filed: Dec. 15, 2011

(86) PCT No.: PCT/US2011/065021
§ 371 (c)(1),
(2), (4) Date: Jun. 4, 2014

(87) PCT Pub. No.: WO2013/089719
PCT Pub. Date: Jun. 20, 2013

(65) Prior Publication Data
US 2014/0328772 A1 Nov. 6, 2014

(51) Int. Cl.
| | | |
|---|---|---|
| *A61Q 11/00* | (2006.01) | |
| *A61Q 19/00* | (2006.01) | |
| *A61K 8/97* | (2006.01) | |
| *A61K 36/575* | (2006.01) | |
| *A01N 31/08* | (2006.01) | |
| *A61K 8/34* | (2006.01) | |
| *A61K 8/49* | (2006.01) | |
| *A61Q 19/10* | (2006.01) | |
| *A01N 25/02* | (2006.01) | |
| *A61Q 11/02* | (2006.01) | |
| *A61K 8/86* | (2006.01) | |

(52) U.S. Cl.
CPC ............ *A01N 31/08* (2013.01); *A01N 25/02* (2013.01); *A61K 8/347* (2013.01); *A61K 8/4973* (2013.01); *A61K 8/4993* (2013.01); *A61K 8/86* (2013.01); *A61Q 11/00* (2013.01); *A61Q 11/02* (2013.01); *A61Q 19/10* (2013.01); *A61K 2800/49* (2013.01)

(58) Field of Classification Search
CPC ............ A61K 2300/00; A61K 36/575; A61K 2800/49; A61K 8/97; A61Q 11/00; A61Q 19/00

See application file for complete search history.

(56) References Cited

U.S. PATENT DOCUMENTS

2009/0087501 A1 * 4/2009 Cummins ..................... 424/729

FOREIGN PATENT DOCUMENTS

| | | |
|---|---|---|
| CN | 101721336 | 6/2010 |
| CN | 102228452 | 11/2011 |
| CN | 102247431 | 11/2011 |
| DE | 102010015791 | 10/2011 |
| DE | 102010015792 | 10/2011 |
| JP | 07033624 A * | 2/1995 |
| JP | 07033649 A * | 2/1995 |
| WO | WO 9834591 A1 * | 8/1998 |
| WO | WO2011106003 | 9/2011 |
| WO | WO2011106492 | 9/2011 |
| WO | WO2011106493 | 9/2011 |

OTHER PUBLICATIONS

International Search Report and the Written Opinion issued in International Application PCT/US11/65021 mailed Oct. 30, 2012. WO.
Written Opinion of the International Preliminary Examining Authority issued in International Application PCT/US11/65021 mailed Jan. 10, 2014. WO.

* cited by examiner

*Primary Examiner* — Frederick Krass
*Assistant Examiner* — Tracy Liu

(57) ABSTRACT

A composition comprising a solubilized magnolol analog comprising at least one magnolol analog chosen from propyl magnolol, isopropyl magnolol, butyl magnolol, and isobutyl magnolol and a sorbitan ester. These solubilized analogs are useful in personal care, oral care, and home care compositions to provide anti-bacterial activity and reducing the expression of pro-inflammatory mediators. If isopropyl is selected, then the sorbitan ester is at least one of polyoxyethylene 20 sorbitan monooleate, and a proviso that if isobutyl magnolol is selected, then the sorbitan ester is poloxyethylene 20 sorbitan monooleate.

11 Claims, No Drawings

SOLUBILIZED MAGNOLOL ANALOGS

CROSS-REFERENCE TO RELATED PATENT APPLICATIONS

The present application is a U.S. national stage entry under 35 U.S.C. §371 of Patent Cooperation Treaty Patent Application No. PCT/US2011/65021, filed Dec. 15, 2011, the entirety of which is incorporated herein by reference.

FIELD OF THE INVENTION

Disclosed are solubilized magnolol analogs.

BACKGROUND OF THE INVENTION

Magnolol analogs, such a propyl magnolol, isopropyl magnolol, butyl magnolol, and isobutyl magnolol, are known to have anti-bacterial activities and they are also shown to be capable of reducing the expression of pro-inflammatory mediators in oral tissues. The problem with using these magnolol analogs is their solubility in typical personal care, oral care, or home care compositions. Their use has been limited by their solubility. It would be desirable to solubilize these analogs to increase their use in personal, oral, or home care compositions. The problem is finding materials that can solubilize these analogs. Even in a given class of material, not all members of the class are effective at solubilizing these analogs.

BRIEF SUMMARY OF THE INVENTION

A composition comprising a solubilized magnolol analog comprising at least one magnolol analog chosen from propyl magnolol, isopropyl magnolol, butyl magnolol, and isobutyl magnolol, a sorbitan ester, with a proviso that if isopropyl magnolol is selected, then the sorbitan ester is at least one of polyoxyethylene 20 sorbitan monolaurate and polyoxyethylene 20 sorbitan monooleate, and a proviso that if isobutyl magnolol is selected, then the sorbitan ester is polyoxyethylene 20 sorbitan monooleate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

Disclosed is a composition comprising a solubilized magnolol analog comprising at least one magnolol analog chosen from propyl magnolol, isopropyl magnolol, butyl magnolol, and isobutyl magnolol, a sorbitan ester, with a proviso that if isopropyl magnolol is selected, then the sorbitan ester is at least one of polyoxyethylene 20 sorbitan monolaurate and polyoxyethylene 20 sorbitan monooleate, and a proviso that if isobutyl magnolol is selected, then the sorbitan ester is polyoxyethylene 20 sorbitan monooleate.

Propyl magnolol is 5,5'-di-n-propylbiphenyl-2,2'-diol, and butyl magnolol is 5,5'-di-n-butylbiphenyl-2,2'-diol. Isopropyl magnolol is 5,5'-di-isopropylbiphenyl-2,2'-diol, and isobutyl magnolol is 5,5'-di-isobutylbiphenyl-2,2'-diol.

Sorbitan esters are known generically as polysorbates, and they can be purchased under the Tween trademark from ICI Americas, Inc. Polysorbates that can be used include, but are not limited to, polysorbate 20 (polyoxyethylene (20) sorbitan monolaurate), polysorbate 40 (polyoxyethylene (2) sorbitan monopalmitate), polysorbate 60 (polyoxyethylene (20) sorbitan monostearate), polysorbate 80 (polyoxyethylene (20) sorbitan monooleate), and polysorbate 85 (polyoxyethylene (20) sorbitan trioleate).

Each of the sorbitan esters is capable of solubilizing up to 100 g per liter of neat propyl magnolol or butyl magnolol. In certain embodiments, the amount of sorbitan ester is at least 10 times the weight of the propyl magnolol or butyl magnolol in the composition.

Polysorbate 80 is capable of solubilizing up to 50 g per liter of neat isopropyl magnolol or isobutyl magnolol. In certain embodiments, the amount of polysorbate 80 is at least 20 times the weight of the isopropyl magnolol or isobutyl magnolol in the composition. It was surprising that polysorbate 80 was able to solubilize these analogs. Isobutyl magnolol is not soluble in polysorbate 20, polysorbate 40, or polysorbate 85.

Polysorbate 20 is capable of solubilizing up to 100 g per liter of neat isopropyl magnolol. In certain embodiments, the amount of polysorbate 20 is at least 10 times the weight of the isopropyl magnolol in the composition. It was surprising that polysorbate 20 was able to solubilize these analogs. Isopropyl magnolol is only soluble up to 10 g per liter in polysorbate 40 or polysorbate 85.

It was surprising that these sorbitan esters were capable of solubilizing these analogs. Many other solubilizers, such as PEG-7 glyceryl cocoate, poloxamer 124, PPG-2 hydroxyethyl cocoamide, PPG-5 laureth-5 (Eumulgin™ ES), PEG-8/SMDI copolymer, isopropyl myristate, or C12-15 alkyl benzoate are not able to solubilize isobutyl magnolol.

The amount of magnolol analog in the composition can be any desired amount. In certain embodiments, the amount is 0.01 to 5% by weight of the composition. In other embodiments, the amount is at least 0.05, at least 0.1, at least 0.2, at least 0.3, at least 0.4, at least 0.5, or at least 1% by weight up to 5% by weight of the composition. In other embodiments, the amount is any of the foregoing minimum amounts up to 4, up to 3, up to 2, or up to 1% by weight of the composition. The weight of the sorbitan ester is then the amount to solubilize the analog with the minimum amount of the sorbitan ester being based on the maximum solubility of the analog in the sorbitan ester. In certain embodiments, the amount of the magnolol analog is 0.1, 0.2, 0.3, 0.4, or 0.5% by weight.

These solubilized analogs are useful in personal care, oral care, and home care compositions. Examples of personal care compositions include, but are not limited to, body wash/shower gel, liquid hand cleanser, bar soap, shampoo, conditioner, antiperspirant/deodorants, and cosmetics. Examples of oral care compositions include, but are not limited to, dentifrices, toothpastes, tooth powders, prophylaxis pastes, mouth rinses, lozenges, gums, gels, paints, confectionaries, and denture cleaners. Examples of oral care compositions that can include solubilized magnolol analogs can be found in WO2011/106492. Examples of home care compositions include, but are not limited to, dish liquids, dish pastes, hard surface cleaners, fabric conditioners, and laundry detergents.

In certain embodiments, the magnolol analog can be present in a body wash/shower gel, liquid hand cleanser, or shampoo in which each of these compositions include a surfactant. The magnolol analog can also be included in a soap (fatty acid soap), which can be in the shape of a bar soap.

EXAMPLES

The following are non-limiting prophetic examples of compositions that can include solubilized magnolol analogs.

| Liquid Cleanser (Body Wash or Liquid Hand Soap) | |
| --- | --- |
| Ingredient Name | % Wt. Range |
| Propyl magnolol or butyl magnolol | 0.01-1% |
| Sorbitan Ester | At least 10 times the weight of the magnolol analog |
| Polyquaternium-7 | 0-0.25 |
| SO$_3$Na Pareth 145-2EO Sulfate | 8-12 |
| Cocamidopropyl Betaine | 2.5-7 |
| Decyl Glucoside | 0-2 |
| Demineralized Water and minors | Q.S. |
| Total Materials | 100 |

| Bar Soap | |
| --- | --- |
| Ingredient Name | % Wt. Range |
| Propyl magnolol or butyl magnolol | 0.01-1% |
| Sorbitan Ester | At least 10 times the weight of the magnolol analog |
| Fatty acid soap | 75-85 |
| Demineralized Water and minors | Q.S. |
| Total Materials | 100 |

| Oral Care Composition | |
| --- | --- |
| Ingredient | Weight % |
| Purified water | Q.S. |
| Sorbitol | 19.45 |
| Glycerin | 20 |
| Sodium CMC-12 type USP | 1.1 |
| Iota carrageenan (LB 9505) | 0.4 |
| Sodium saccharin-USP | 0.3 |
| Sodium fluoride | 0.24 |
| Zeodent-115-dental type silica abrasive | 8.5 |
| Zeodent-165-synthetic amorphous PPT silica | 3 |
| Dental type silica sylodent XWA650 | 10 |
| Titannium dioxide (TiO2) | 0.5 |
| Sodium lauryl sulphate powder-NF | 1.5 |
| Flavor | 1 |
| Propyl magnolol or butyl magnolol | 0.01-1% |
| Sorbitan ester | At least 10 times the weight of the magnolol analog |
| Total | 100 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A composition comprising a solubilized magnolol analog comprising:
    at least one magnolol analog chosen from propyl magnolol, isopropyl magnolol, butyl magnolol, and isobutyl magnolol,
    a sorbitan ester,
    with a proviso that if isopropyl magnolol is selected, then the sorbitan ester is at least one of polyoxyethylene 20 sorbitan monolaurate and polyoxyethylene 20 sorbitan monooleate, and a proviso that if isobutyl magnolol is selected, then the sorbitan ester is polyoxyethylene 20 sorbitan monooleate;
    wherein the magnolol analog is present in an amount of 0.01 to 5% by weight of the composition; and wherein the composition comprises:
    (a) Isopropyl magnolol and 10 times its weight of polyoxyethylene 20 sorbitan monolaurate; or
    (b) Isopropyl magnolol and 20 times its weight of polyoxyethylene 20 sorbitan monooleate; or
    (c) Isobutyl magnolol and 20 times its weight of polyoxyethylene 20 sorbitan monooleate; or
    (d) Propyl magnolol and 10 times its weight of polyoxyethylene 20 sorbitan monolaurate, polyoxyethylene 20 sorbitan monopalmitate, polyoxyethylene 20 sorbitan monooleate, or polyoxyethylene sorbitan trioleate; or
    (e) Butyl magnolol and 10 times its weight of polyoxyethylene 20 sorbitan monolaurate, polyoxyethylene 20 sorbitan monopalmitate, polyoxyethylene 20 sorbitan monooleate, or polyoxyethylene sorbitan trioleate.

2. The composition of claim 1 further comprising a surfactant.

3. The composition of claim 1 further comprising soap.

4. The composition of claim 3 in the form of a bar soap.

5. The composition of claim 2 in the form of a liquid cleanser.

6. The composition of claim 1 in the form of an oral care composition.

7. The composition of claim 1, wherein the composition comprises propyl magnolol and 10 times its weight of polyoxyethylene 20 sorbitan monolaurate, polyoxyethylene 20 sorbitan monopalmitate, polyoxyethylene 20 sorbitan monooleate, or polyoxyethylene sorbitan trioleate.

8. The composition of claim 1, wherein the composition comprises isopropyl magnolol and 10 times its weight of polyoxyethylene 20 sorbitan monolaurate.

9. The composition of claim 1, wherein the composition comprises butyl magnolol and 10 times its weight of polyoxyethylene 20 sorbitan monolaurate, polyoxyethylene 20 sorbitan monopalmitate, polyoxyethylene 20 sorbitan monooleate, or polyoxyethylene sorbitan trioleate.

10. The composition of claim 1, wherein the composition comprises isobutyl magnolol and 20 times its weight of polyoxyethylene 20 sorbitan monooleate.

11. The composition of claim 1, wherein the the composition comprises isopropyl magnolol and 20 times its weight of polyoxyethylene 20 sorbitan monooleate.

* * * * *